United States Patent [19]
Boukhny et al.

[11] Patent Number: 5,676,649
[45] Date of Patent: Oct. 14, 1997

[54] PHACOEMULSIFICATION CUTTING TIP

[75] Inventors: Mikhail Boukhny, Laguna Beach; James Y. Chon, Chino Hills, both of Calif.

[73] Assignee: Alcon Laboratories, Inc., Fort Worth, Tex.

[21] Appl. No.: 723,665

[22] Filed: Oct. 4, 1996

[51] Int. Cl.⁶ ..................... A61B 17/00
[52] U.S. Cl. ..................... 604/22; 606/169
[58] Field of Search ............. 604/22; 606/166, 606/170, 169, 171, 180

[56] References Cited

U.S. PATENT DOCUMENTS

| | | |
|---|---|---|
| 3,589,363 | 6/1971 | Banko et al. |
| 4,169,984 | 10/1979 | Parisi. |
| 4,223,676 | 9/1980 | Wuchinich et al. |
| 4,246,902 | 1/1981 | Martinez. |
| 4,493,694 | 1/1985 | Wuchinich. |
| 4,515,583 | 5/1985 | Sorich. |
| 4,589,415 | 5/1986 | Haaga. |
| 4,609,368 | 9/1986 | Dotson, Jr. |
| 4,634,419 | 1/1987 | Kreizman et al. |
| 4,634,420 | 1/1987 | Spinosa et al. |
| 4,869,715 | 9/1989 | Sherburne. |
| 4,922,902 | 5/1990 | Wuchinich et al. |
| 4,974,581 | 12/1990 | Wiksell. |
| 4,989,583 | 2/1991 | Hood. |
| 4,989,588 | 2/1991 | Kubota et al. |
| 5,154,694 | 10/1992 | Kelman. |
| 5,199,943 | 4/1993 | Wypych ............ 606/169 |
| 5,324,297 | 6/1994 | Hood et al. ........ 604/22 |
| 5,359,996 | 11/1994 | Hood. |
| 5,531,722 | 7/1996 | Van Hale .......... 604/22 |

*Primary Examiner*—William Lewis
*Attorney, Agent, or Firm*—Jeffrey S. Schira

[57] ABSTRACT

A cutting tip having an asymmetric, hydrodynamic channel that tightens the cutting tip during operation.

3 Claims, 3 Drawing Sheets

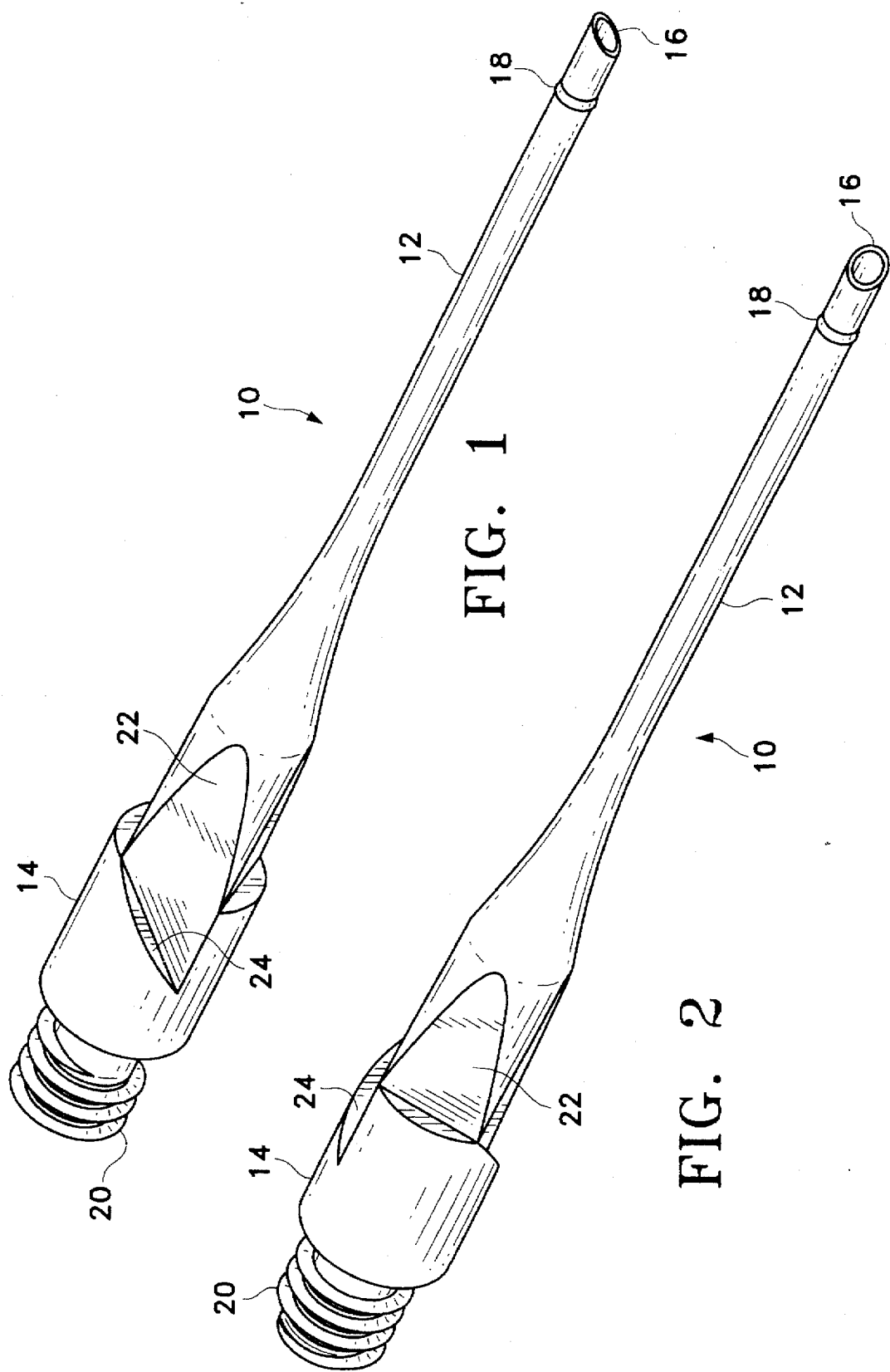

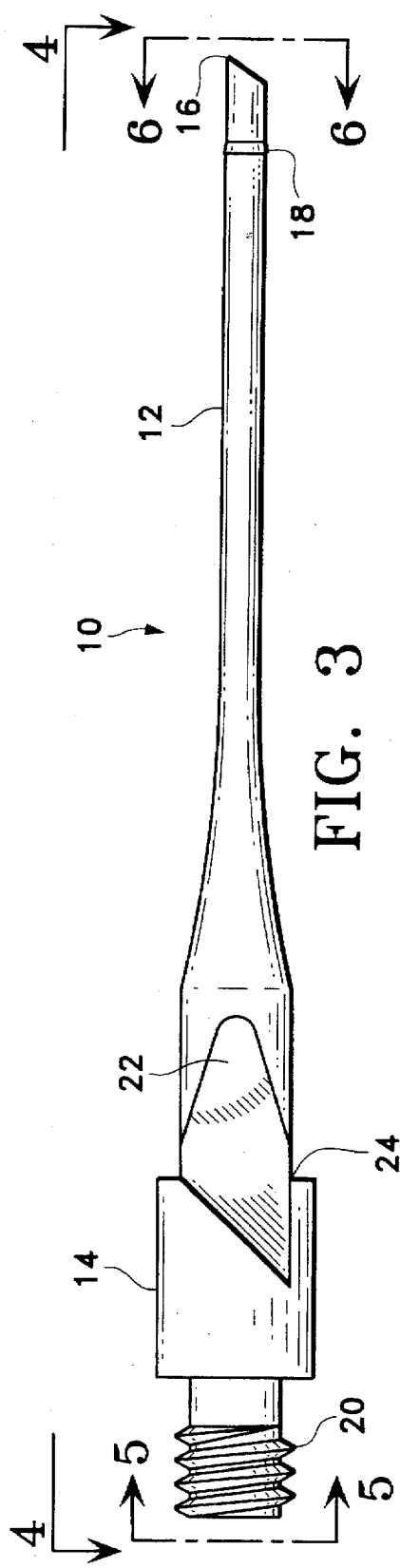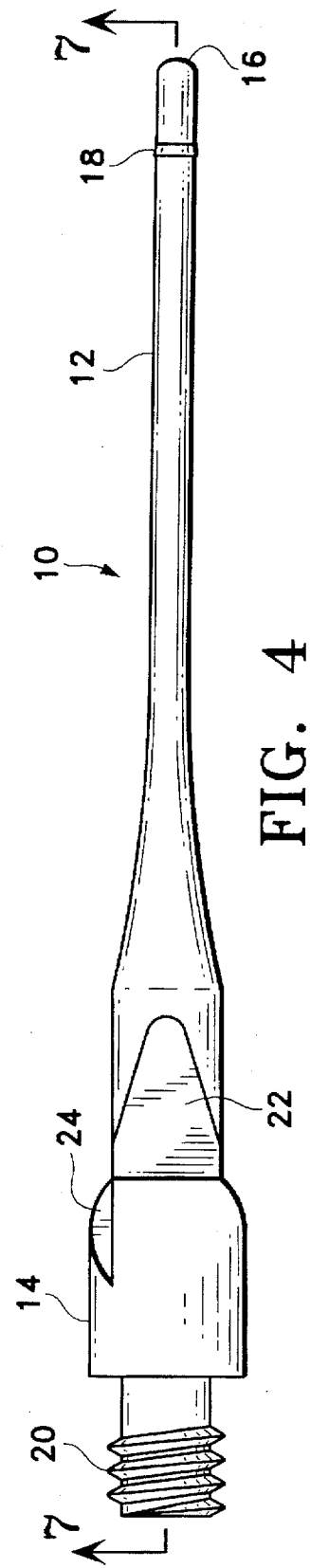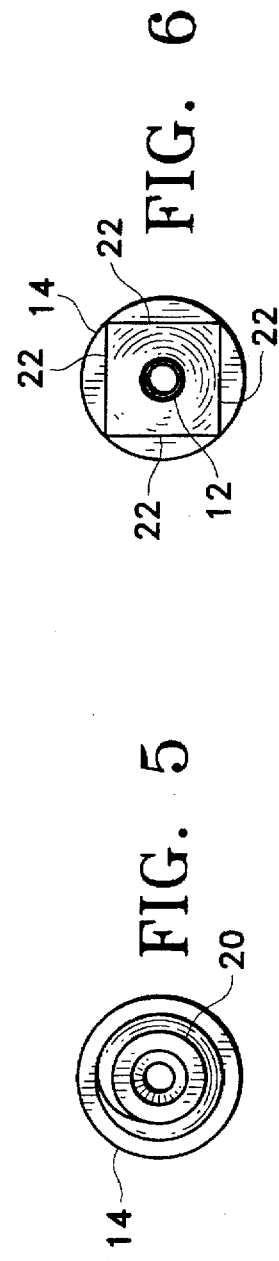

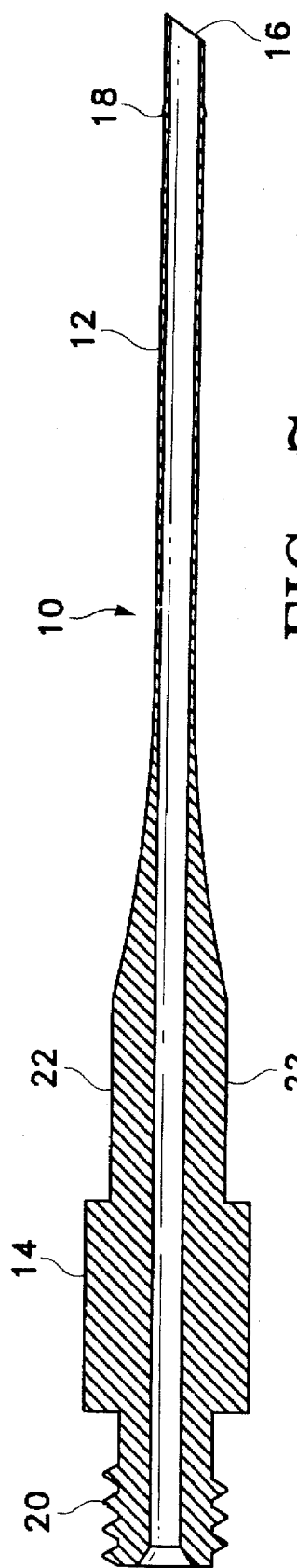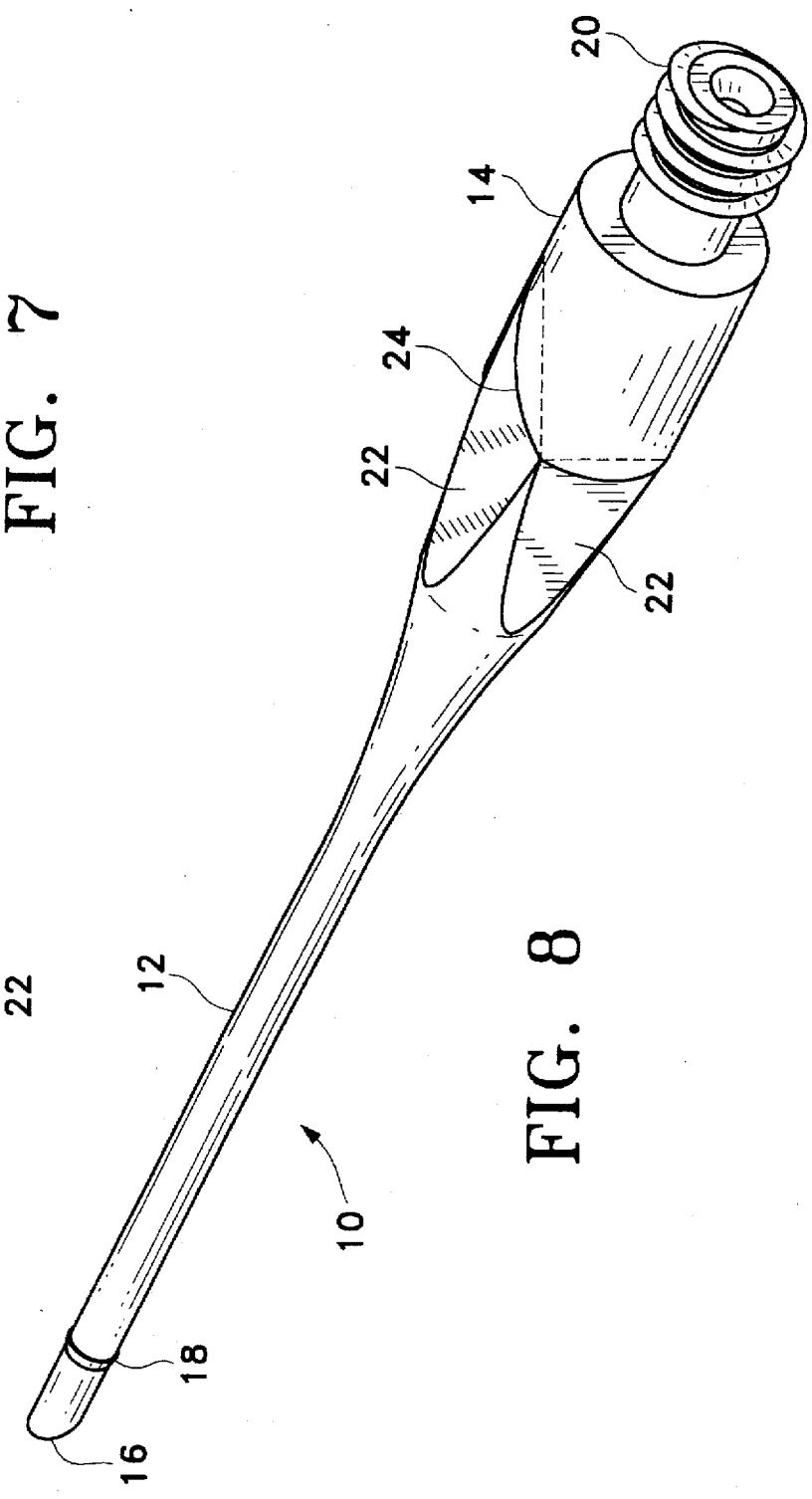
FIG. 7
FIG. 8

PHACOEMULSIFICATION CUTTING TIP

BACKGROUND OF THE INVENTION

This invention relates generally to the field of phacoemulsification and more particularly to phacoemulsification cutting tips.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an IOL.

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is eternally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

The horn (transducer) assembly, including both piezoelectric and high endurance limit inert materials, used in ultrasonic handpieces must be carefully tuned for proper operation. As used herein, "tuning" is the process of finding and tracking the correct resonant frequency of the handpiece operating under loaded or unloaded conditions. Operating the handpiece at resonance takes advantage of the transducer's energy storage capabilities, which occurs only at resonance. With proper tuning, the transducer will store mechanical energy while operating unloaded and release this energy into the material being cut when loaded. As a consequence, for short periods of time, large amounts of energy can be directed into the material by the transducer itself and not by the transducer's power source. This allows the power source to be designed to handle only the steadystate power requirement of the transducer and not the loaded transients which can be many times higher.

The usual way of determining the resonant frequency of a transducer is to compare the phase angle between the voltage applied to the transducer and the current drawn by the transducer. When alternating voltage is applied to a circuit, current will flow through the circuit. The amount of current is determined by dividing the voltage by the impedance of the circuit according to Ohm's Law. If the circuit is purely resistive, the impedance is equal to the total resistance in the circuit and the current equals the voltage divided by the circuit resistance.

When the voltage and current waveforms are viewed on an oscilloscope for a particular circuit, if the circuit is inductive, current will lag voltage and, if the circuit is capacitive, the voltage will lag the current. The time difference between the points when the voltage and current waveforms intersect the zero axis is measured in trigonometric terms by the phase angle $\phi$. For purely resistive circuits, $\phi=0$ and the voltage and the current are said to be in phase. For purely inductive circuits $\phi=90°$ and for purely capacitive circuits, $\phi=-90°$ and the voltage and the current are said to be out of phase.

For circuits containing all three elements, resistors, inductors and capacitors, there will be some frequencies where the total impedance of the circuit will appear purely resistive even though the circuit contains reactive elements. These frequencies are the resonant frequencies. Consequently, one method of determining the resonant frequencies of a complex circuit is to apply an alternating voltage to the circuit and vary the frequency until the phase angle $\phi$ between the voltage and current is zero. The frequencies where this condition occurs are the resonant frequencies. As discussed above, when driving a circuit having both resistive and reactive components, it is important to know the value of the phase angle $\phi$ because the power absorbed by the circuit is directly proportional to the cosine of the phase angle (cos ($\phi$)). For a phase angle equal to zero, cos(0)=1 (unity) and the transfer of power from the source to the circuit is at a maximum, this is the case for purely resistive loads. However, if $\phi=90°$ or if $\phi=-90°$, as is the case for reactive loads, the cos($\phi$)=0 so there is no power transferred through the circuit. Cos($\phi$) is referred to as the power factor.

Ultrasonic devices driven by piezoelectric of magnorestrictive elements present complex equivalent circuits that are a combination of capacitors, inductors and resistors and generally have more than one resonant frequency. In fact, for these electromechanical transducers, the resonant frequencies occur in pairs of closely spaced frequencies where the impedance is resistive and the phase angle φ is zero. One of these resonant frequencies is called the series resonant frequency and the other resonant frequencies is called the parallel resonant frequency or the antiresonance. When the ultrasonic device is driven at either of these frequencies the power factor is equal to unity and the transfer of power is maximized.

In order to tune piezoelectric handpiece properly, it is important for the cutting tip to be attached firmly to the ultrasonic horn. If the cutting tip becomes loose, the handpiece will go out of tune, and not operate efficiently.

Therefore, a need continues to exist for a phacoemulsification cutting tip that resists becoming loose from the ultrasonic horn.

BRIEF SUMMARY OF THE INVENTION

The present invention improves upon the prior art by providing a cutting tip having an asymmetric, hydrodynamic channel that tightens the cutting tip during operation.

Accordingly, one objective of the present invention is to provide a phacoemulsification cutting tip that resists loosening during operation.

Another objective of the present invention is to provide a phacoemulsification cutting tip having a hydrodynamic shape.

Another objective of the present invention is to provide a phacoemulsification cutting tip having an asymmetrical shape.

These and other advantages and objectives of the present invention will become apparent from the detailed description and claims that follow.

BRIEF DESCRIPTION OF THE DRAWINGS

FIG. 1 is a perspective view of the phacoemulsification cutting tip of the present invention.

FIG. 2 is a perspective view of the phacoemulsification cutting tip of the present invention similar to FIG. 1 but with the cutting tip rotated 90°.

FIG. 3 is a top plan view of the phacoemulsification cutting tip of the present invention.

FIG. 4 is a side elevational view of the phacoemulsification cutting tip of the present invention taken along line 4—4 in FIG. 3.

FIG. 5 is an end elevational view of the phacoemulsification cutting tip of the present invention taken along line 5—5 in FIG. 3.

FIG. 7 is an end elevational view of the phacoemulsification cutting tip of the present invention taken along line 6—6 in FIG. 3.

FIG. 7 is a cross-sectional view of the phacoemulsification cutting tip of the present invention taken along line 7—7 in FIG. 4.

FIG. 8 is a perspective view of the phacoemulsification cutting tip of the present invention taken from a direction opposite the direction taken in FIGS. 1 and 2.

DETAILED DESCRIPTION OF THE INVENTION

Phacoemulsification cutting tip 10 of the present invention generally includes shaft 12 integrally formed with hub 14 at the proximal end of shaft 12. Cutting tip 10 is preferably made from stainless steel or titanium, but other materials may also be used. Cutting tip 10 preferably has an overall length of between 1.00 inches and 1.50 inches, with 1.325 inches being most preferred. Cutting tip 10 may be formed using conventional metalworking technology and preferably is electropolished to remove any burrs.

Shaft 12 is generally tubular, with an outside diameter of between 0.005 inches and 0.100 inches and an inside diameter of between 0.001 inches and 0.090 inches. Distal end 16 of shaft 12 may be cut square, or as shown in FIGS. 1, 2, 3 and 8, cut at any suitable angle between 0° and 90°. Shaft 12 may also contain stop 18 that prevents sleeves or other items (not shown) installed in cutting tip 10 from sliding off of shaft 12.

Hub 14 includes threaded portion 20 that allows cutting tip 10 to be attached to an ultrasonic horn (not shown). Hub 14 also includes wrenching flats 22 that permit a wrench (not shown) to engage cutting tip 10. Suitable wrenches are more fully described in U.S. Pat. No. Des. 351,095, the entire contents of which is incorporated herein by reference. Hub 14 preferably has an overall diameter of between 0.100 inches and 0.150 inches with 0.140 inches being most preferred. As best seen in FIGS. 1 and 3, hub 14 also contains a pair of asymmetric, hydrodynamic channels 24 extending from flats 22. Channels 24 preferably are cut at an angle of 45° relative to the longitudinal axis of cutting tip 10, but channels 24 may be of any suitable number, size or shape as may be required to produce the desired tightening or untightening effect.

In use, as cutting tip 10 vibrates in a liquid medium, the hydrodynamic forces acting on channels 24 vary as cutting tip 10 moves forward and backward. As cutting tip 10 moves forward, the increased hydrodynamic forces on channels 24 tend to rotate hub 14 clockwise (as seen in FIG. 6). As cutting tip 10 moves backward, the reduced pressure around channels 24 tend to rotated hub 14 counterclockwise. The net result, however, is an overall clockwise turning of hub 14 because negative pressure exerted on channels 24 on the backward stroke can never fall below negative 1 bar relative to atmosphere but increased pressure exerted on channels 24 on the forward stroke can elevate to very high levels.

This description is given for purposes of illustration and explanation. It will be apparent to those skilled in the relevant art that changes and modifications may be made to the invention described above without departing from its scope or spirit. For example, by changing the size, shape location or number of channels 24, the overall effect of the hydrodynamic forces acting on channels 24 may be increased, decreased or counterclockwise, if such an effect is desired.

We claim:

1. A phacoemulsification tip, comprising:
   a) a tubular shaft having a longitudinal axis, a distal end and a proximal end; and
   b) a hub connected to the shaft at the distal end, the hub containing at least one wrenching flat and at least one hydrodynamic channel, the channel being asymmetric about the longitudinal axis.

2. The cutting tip of claim 1 wherein the hub contains a pair of asymmetric, hydrodynamic channels.

3. The cutting tip of claim 1 wherein the hydrodynamic channel is cut into the hub at the wrenching flat and at an angle of approximately 45 degrees relative to the longitudinal axis.

* * * * *